United States Patent [19]
Hambitzer et al.

[11] Patent Number: 5,932,791
[45] Date of Patent: Aug. 3, 1999

[54] METHOD AND APPARATUS FOR THE CONTINUOUS DETERMINATION OF GASEOUS OXIDATION PRODUCTS

[75] Inventors: Günther Hambitzer, Pfinztal; Bernhard Beurer, Karlsruhe; Wolfgang Liehmann, Walzbachtal, all of Germany

[73] Assignee: Fraunhofer-Gesellschaft zur Forderung der angewandten Forschung, Munich, Germany

[21] Appl. No.: 08/848,562

[22] Filed: Apr. 28, 1997

[30] Foreign Application Priority Data

Apr. 26, 1996 [DE] Germany .................. 196 16 760

[51] Int. Cl.[6] .............. G01N 7/00; G01N 31/12; B01D 21/00; C12P 7/42
[52] U.S. Cl. .............. 73/19.01; 436/146; 422/78; 210/711
[58] Field of Search .............. 73/19.01; 436/146; 422/78, 80; 210/761, 762

[56] References Cited

U.S. PATENT DOCUMENTS

| | | | |
|---|---|---|---|
| 3,840,341 | 10/1974 | Rogers | 436/146 |
| 3,955,924 | 5/1976 | Northmore et al. | 436/146 |
| 4,141,829 | 2/1979 | Reinhard et al. | 210/762 |
| 4,277,438 | 7/1981 | Ejzak | 422/80 |
| 4,293,522 | 10/1981 | Winkler | 422/80 |
| 4,694,682 | 9/1987 | Heikkila et al. | 73/61.53 |
| 5,132,094 | 7/1992 | Godec et al. | 422/68.1 |
| 5,292,666 | 3/1994 | Fabinski et al. | 436/114 |
| 5,340,542 | 8/1994 | Fabinski et al. | 422/82.05 |
| 5,394,733 | 3/1995 | Acholla | 73/23.41 |
| 5,413,763 | 5/1995 | Jeffers | 422/80 |
| 5,443,991 | 8/1995 | Godec et al. | 436/145 |
| 5,672,516 | 9/1997 | Jeffers | 436/146 |

Primary Examiner—Hezron Williams
Assistant Examiner—Jay L. Politzer
Attorney, Agent, or Firm—Antonelli, Terry, Stout & Kraus, LLP

[57] ABSTRACT

A method is proposed for the contiuous determination of gaseous oxidation products from industrial process, drinking and/or waste water, particularly for determining the TOC value, at least the organically bound carbon contained in a test solution to be investigated being oxidatively transformed and the gaseous oxidation products are supplied to a measuring unit, where at least the organically bound carbon is detected, the test solution being continuously pumped into a microreactor, where it is heated to a predetermined temperature and the organic compounds in the test solution are continuously oxidatively transformed under a temperature and pressure increased in a defined manner. An apparatus for the continuous determination of gaseous oxidation products from industrial process, drinking and waste water, particularly for determining the TOC value, having an oxidation unit and a following measuring unit has a terminally open heatable microreactor as the oxidation unit, upstream of which is provided a high pressure pump for the continuous supply of the test solution.

13 Claims, 3 Drawing Sheets

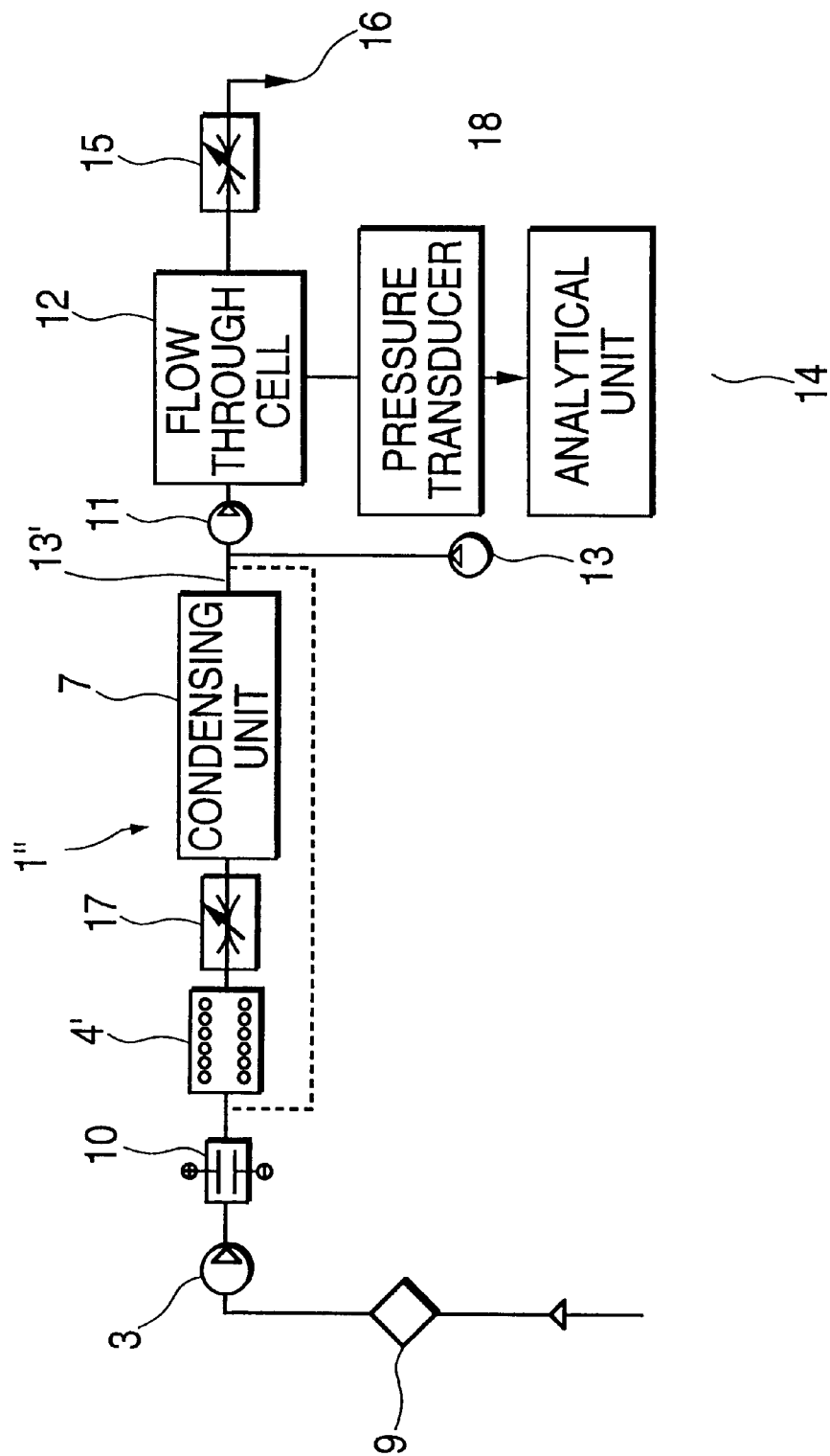

METHOD AND APPARATUS FOR THE CONTINUOUS DETERMINATION OF GASEOUS OXIDATION PRODUCTS

BACKGROUND OF THE INVENTION

The invention relates to a method for the continuous determination of gaseous oxidation products from industrial process, drinking and/or waste water, particularly for determining the TOC value, organically bound carbon contained in a test solution to be investigated being oxidatively transformed and the gaseous oxidation products are supplied to a measuring unit, as well as an apparatus for the continuous determination of gaseous oxidation products from industrial process, drinking and/or waste water, particularly for determining the TOC value, with an oxidation unit and a following measuring unit.

The TOC (total organic carbon) value is an important fundamental quantity relating to the content of organic substances in waste water. In addition, the measurement of this value provides guidance values for determining the COD (chemical oxygen demand) value and BOD (biological oxygen demand) value. Thus, the TOC value is determined in the environmental protection field, particularly the monitoring of waste water or sewage, as well as in process control and monitoring in the industrial sector.

In known apparatuses the determination of the TOC value takes place by means of an oxidative transformation or conversion of the carbon of organic compounds to measurable carbon dioxide. Prior to the actual measurement the test solutions to be investigated must be filtered on sampling and multiphase mixtures have to be processed, in order to prevent in the apparatus any deposits, which lead to a reduction of the detection signal and to the response time.

Apart from inorganic compounds, most of the samples to be investigated also contain carbon-containing inorganic compounds, mainly in the form of carbonates and hydrogencarbonates. The value of the total inorganically bound carbon or total inorganic carbon is known as the TIC value. Frequently the carbon-containing, inorganic compounds are removed prior to the determination of the TOC value, whilst adding acid (pH<2) to the test solution using carbon dioxide-free carrier gas. However, highly volatile hydrocarbons are also stripped. However, if these highly volatile hydrocarbons are to be taken into account during the determination, following the prior separation of the inorganic compounds they must be supplied to the oxidation unit.

The actual oxidative transformation of the organic compounds in most commercially available process TOG equipments takes place by UV irradiation combined with an oxidant or by thermal catalytic oxidation.

Equipments with UV decomposition units are unable to completely convert into carbon dioxide the organically bound carbon of difficultly oxidizable organic compounds. Thus, the organically bound carbon of such compounds can consequently not be detected and leads to diminished values and therefore to uncertain analytical results. With test solutions having a high chloride percentage, UV irradiation also leads to chlorine formation, which once again absorbs UV radiation and reduces the detection sensitivity of the apparatus.

Therefore an increasing use is being made of apparatuses, in which the conversion to carbon dioxide takes place by a catalytically assisted, thermal oxidation. In the case of a suitable choice of the catalyst temperature, as well as an adequate residence time of the sample in the oven, the oxidation is independent of the sample and supplies an almost 100% detection sensitivity for all hydrocarbon compounds. However, it is disadvantageous that the high temperatures necessary for oxidation in the range of 850° C. lead to deposits in the oven unit and therefore to increased wear thereto. Moreover, the catalysts used are platinum (Pt) or palladium (Pd) catalysts, which are expensive and must regularly be replaced. As the oxidation products must be supplied with the aid of a carrier gas flow via corresponding purification stages to a detection unit for carbon dioxide detection, particularly in the case of test solutions with a high proportion of flammable liquids, problems arise during detection, because they can lead to extreme pressure changes in the pressure-dependent oxidation unit. Generally the detectors used are non-dispersive IR detectors, but these are restricted to carbon dioxide detection.

SUMMARY OF THE INVENTION

Whilst avoiding the aforementioned disadvantages, the problem of the invention is to provide a method and apparatus of the aforementioned type allowing a continuous, reliable and simple determination of at least the TOC value in process, drinking and/or waste water.

According to the invention, this problem is solved by a method of the aforementioned type in that the test solution is continuously pumped in a microreactor, is heated in said microreactor to a predetermined temperature and the organic compounds in the test solution are continuously oxidatively transformed under a temperature and pressure increased in a defined manner. An apparatus according to the invention is characterized by a terminally open, heatable microreactor as the oxidation unit, upstream of which is provided a high pressure pump for the continuous supply of the test solution.

It has surprisingly been found that by means of the method and apparatus according to the invention a continuous transformation of organic compounds, including difficultly oxidizable organic compounds is possible. The temperature necessary for the transformation is brought about by heating the microreactor. The elevated pressure necessary for the transformation is preferably built up by the evaporation pressure of the test solution. For this purpose the microreactor is constructed in a substantially tubular manner, preferably in the form of a small diameter capillary tube. In this way the pressure build-up in the microreactor or capillary tube takes place continuously through the rapid evaporation of the heated test solution and the vapor pressure resulting therefrom. The microreactor can be directly or indirectly heated for this purpose. For this purpose the capillary tube is either itself constructed as a heating resistor or is in heat conducting connection with the heater material of a resistance heating means.

For the detection of the oxidation products formed, the sample to be investigated is directly and continuously oxidatively transformed under supercritical conditions. There is no need for a carrier gas flow for transporting the sample through the oxidation unit and to the detector, because the volatile oxidation products are directly determined from the sample without prior phase transfer. An oxidation temperature of approximately 400° C. is sufficient, whereas the temperatures in the case of catalytic combustion are higher. Higher temperatures are conceivable if the reaction capillaries have an adequate thermal stability and corrosion resistance. A pressure of approximately 250 bar is adequate for the oxidation of organic compounds.

According to a further development oxygen is supplied to the test solution. The oxygen can be supplied before or during oxidative transformation. This ensures a complete transformation of all the organic compounds in the test solution. The oxygen is preferably generated electrochemically, but a supply using external gas feeds is also possible. The electrochemical oxygen generation can take place directly in the interior of the reactor through electrodes with a corresponding geometry, or outside the same. As a result of the reaction conditions (pressure, temperature) within the microreactor, the organic compounds in the test solution and oxygen supplied are completely dissolved. As the oxidative transformation takes place in a one-phase system, it is easier to control the reaction conditions than in known combustion reactions. As the oxygen is preferably supplied in excess, the organic compounds are oxidized to carbon dioxide and water. Any heteroatoms contained in the hydrocarbon compounds (sulphur, halogens and nitrogen) are converted into the corresponding mineral acids.

Subsequently the test solution transferred into the gaseous phase is preferably condensed. The condensed sample in further-forming manner is passed at a constant flow rate through a flow-through cell. Beforehand acid is preferably dosed into the same to ensure that hydrogencarbonate and carbonate contained in the condensed sample is converted into free carbon dioxide (free carbonic acid). In order to ensure a complete transformation of the hydrogen carbonate and carbonate, the pH-value after acid addition should be pH=2. As the concentration of the free carbonic acid and the concentration of the carbonates and hydrogencarbonates are directly dependent on the pH-value and only gaseous substances can be detected with the method and apparatus according to the invention, for determining the carbon dioxide the pH-value must be known or kept constant. In the case of a non-constant pH-value, carbon dioxide determination can alternatively take place through the measurement of the free carbonic acid (carbon dioxide) and a measurement of the pH-value.

In order now to supply the gaseous oxidation products to an analytical or detection unit, the condensed sample is moved past a liquid-impermeable, but gas-permeable membrane, the gaseous oxidation products are sucked off in the gas phase from the sample through the membrane and passed through a measuring cell. Preferably the sample in the vicinity of the membrane is kept at a constant temperature and a predetermined pressure. As a result of the clearly defined temperature and pressure conditions in the flow-through cell, the quantity of dissolved carbon dioxide in the condensate, i.e. the condensed sample, is proportional to the gaseous carbon dioxide quantity in the detection unit. A proportion of the gaseous oxidation products to be investigated passes out of an area with a slight underpressure, via a pressure transducer 18 with a shield to the detection unit. The pressure transducer should be kept at the same constant temperature as the flow-through cell. As a result of the underpressure the diffusion behavior of the gaseous oxidation products through the membrane is assisted and intensified.

According to a further development, the gaseous oxidation products are measured by means of a mass spectrometer. The mass spectrometer offers the possibility of also determining other gaseous oxidation products than carbon dioxide, e.g. oxidation products from halogen, sulphur or nitrogen compounds. Following corresponding adaptation, the analytical unit can e.g. also be used for determining the total oxygen content according to Kjeldahl.

For cost reasons, the gaseous oxidation products can also be determined e.g. by means of a non-dispersive infrared detector or a flame ionization detector. However, these gas analyzers are only suitable for the detection of gaseous carbon dioxide.

The apparatus according to the invention preferably uses an electrochemical reactor upstream of the microreactor for oxygen feed or generation. Alternatively, it is possible to have electrodes in the microreactor interior for electrochemical oxygen generation. The oxygen generation can then take place directly in the microreactor interior by electrodes having a corresponding geometry. Apart from the electrochemical generation of oxygen, it is also possible to directly dose in pure oxygen. For this the apparatus then has a gas supply for feeding in oxygen.

Whilst the pressure necessary for oxidative transformation is preferably built up by the evaporation pressure of the test solution in the interior of the capillary tube, in another embodiment, there is a pressure maintaining valve upstream of the microreactor, e.g. a regulating valve. The pressure build-up takes place by reducing the flow cross-section at the open end of the microreactor. When using such a pressure maintaining valve directly behind the microreactor for the pressure build-up, the geometry of the capillary tube or microreactor is variable. In particular, longer reaction times are possible through the enlargement of the reactor volume.

According to a preferred development, the inner tube walls of the microreactor are given a temperature and corrosion-resistant coating. The coating materials can be metal alloys, which have such an adequate thermal stability and corrosion resistance. Preferably use is made of nickel and nickel alloys, as well as tantalum. Apart from chemical stability, such materials also have catalytic properties. However, the inner tube walls can also be coated with other catalyst materials, which have similar properties to those mentioned hereinbefore. For the outer tube walls the thermally stable materials can be specifically thermally stable steels (e.g. Cr-Ni-No steel) or ceramic materials, which have an adequate mechanical strength. When using material combinations, the outer tube wall and capillary tubes are made from the same material.

According to a further development the microreactor is followed by a condenser unit, which can be constructed in the form of an adequately dimensioned condenser for condensing the now gaseous sample.

In order to be able to supply the sample to a detection unit, there is preferably a pumping mechanism for pumping the condensed sample through a flow-through chamber or cell. In order to achieve a continuous flow, it is also possible for the flow-through cell to be followed by a pressure maintaining valve. Thus, a constant pressure is built up between the pump and the open flow-through cell end, e.g. in order to maintain gaseous carbon dioxide in solution.

Preferably, between the condensation unit and the flow-through cell, there is an acid feed location. Due to the resulting possibility of acid dosing, it is ensured that the hydrogencarbonate and carbonate contained in the sample is converted into free carbon dioxide.

In order to supply the gaseous oxidation products contained in the condensed sample to a measuring means, the flow-through cell is preferably separated from a measuring cell by a liquid-impermeable, but gas-permeable membrane. In order to assist the passage of the gaseous oxidation products to be investigated from the condensed sample through the membrane, according to further developments on the flow-through cell is located a regulated heating device and/or on the membrane side remote from said cell is provided at least one pump, which produces a moderate underpressure for the sucking off of at least the gaseous carbon dioxide. As a result of the clearly defined temperature and pressure conditions in the flow-through cell, the dissolved carbon dioxide quantity in the condensed sample is proportional to the gaseous carbon dioxide quantity in the following detection unit.

In an extremely preferred development, a pressure tranducer with an adjustable shield is provided. By means of the latter a partial gaseous oxidation product and in particular gaseous carbon dioxide flow passes to the detection unit. For this purpose, the measuring cell preferably has an electron impact ion source of a quadrupole mass spectrometer. This mass spectrometer offers the possibility of determining other gaseous oxidation products obtained from halogen, sulphur or nitrogen compounds. Following corresponding adaptation, it is e.g. also suitable for determining the total nitrogen content according to Kjeldahl. Through the use of a bypass at the oxidation unit or by rapidly cooling the oxidation unit, apart from gaseous oxidation products, it is also possible to determine gaseous constituents (e.g. chlorinated hydrocarbons, phenols, etc.) in the test solution.

The unit for measuring the gaseous oxidation products can be constituted by the applicant's apparatus known from DE-OS 41 33 300, so that no express details of this apparatus are needed here.

BRIEF DESCRIPTION OF THE DRAWINGS

Further advantages and features of the invention can be gathered from the claims and following description of embodiments with reference to the attached drawings, wherein show:

FIG. 3 A third embodiment of the inventive apparatus in a more detailed diagrammatic representation.

DETAILED DESCRIPTION OF THE PREFERRED EMBODIMENTS

Figure 1:
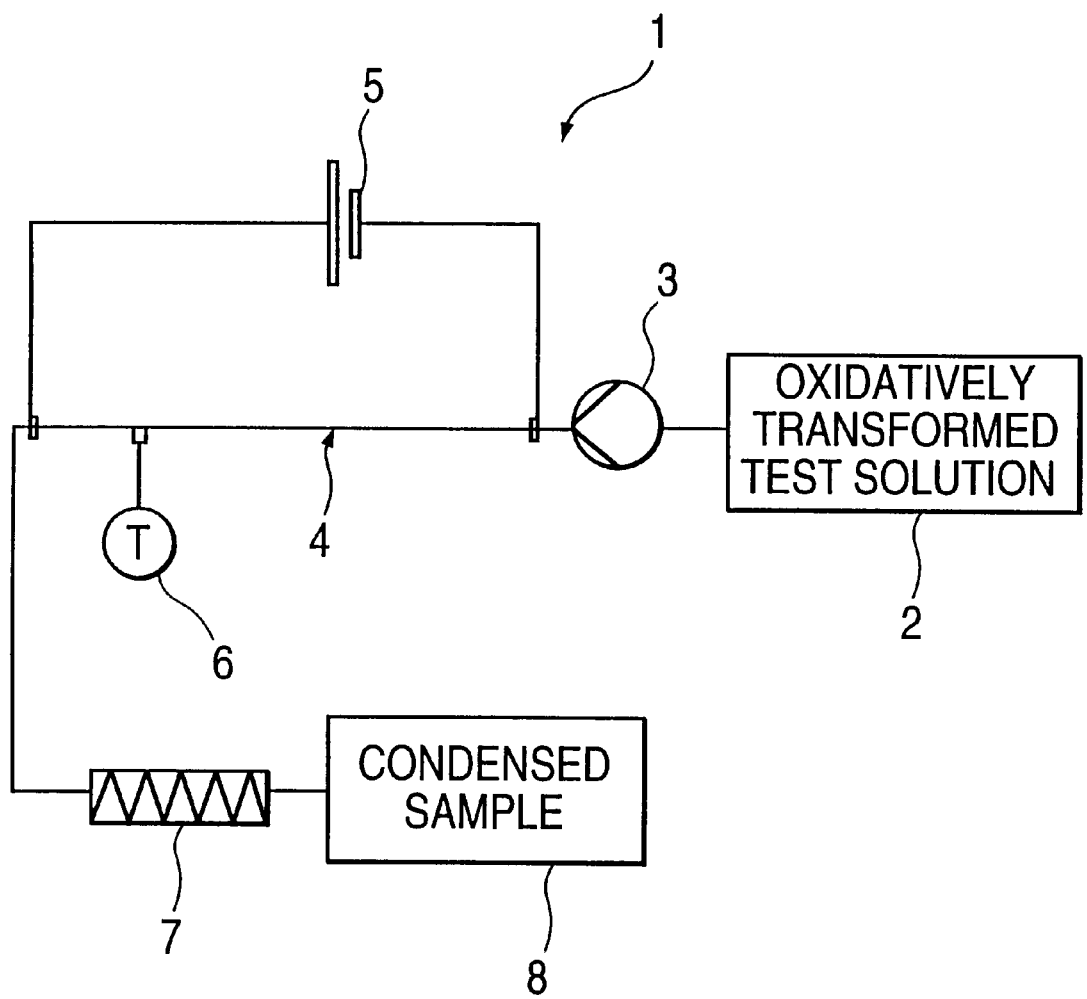
FIG. 1 A diagrammatic representation of the essential components of a first embodiment of a sample preparation system of the inventive apparatus.

The apparatus 1 according to the invention shown in FIG. 1 has a pump 3, with which an oxygen-enriched, aqueous test solution (cf. FIG. 2) of the waste water to be investigated is supplied to a terminally open microreactor 4, such as a reaction capillary. The reaction capillary 4 is made from an electrically resistant material or is coated with such a material on a dielectric, tubular carrier and consequently also serves as a heating resistor. It is connected to a d.c. voltage source 5 by means of which the microreactor 4 is directly heated. For checking and optionally regulating the temperature a thermometer 6 is provided.

The outlet of the microreactor 4 is connected to a condensing vessel 7 in which the oxidatively transformed test solution 2 is condensed. Following condensation in the condensing vessel 7 there is a condensed sample 8 to be supplied to a not shown detection unit.

Figure 2:
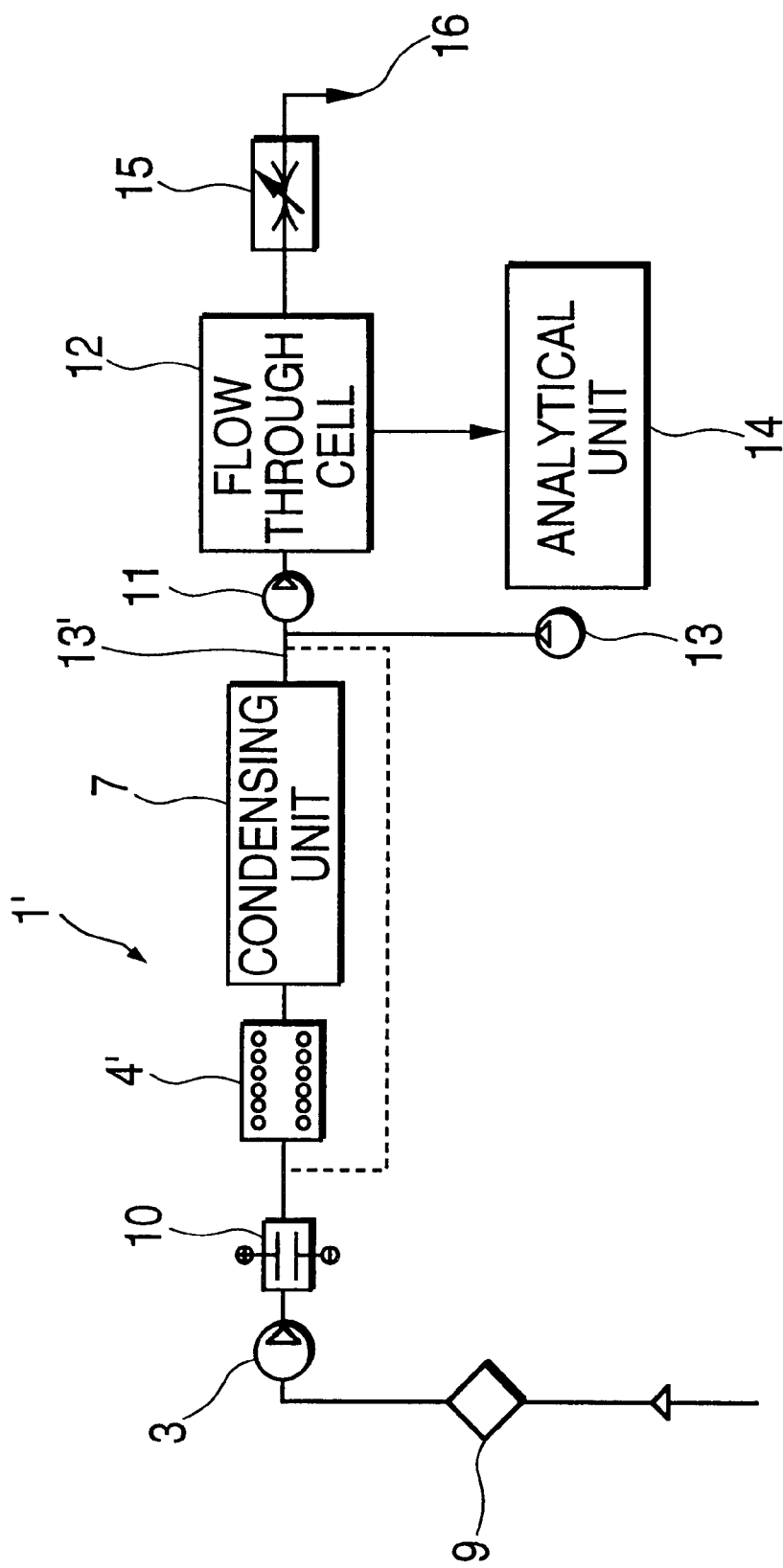
FIG. 2 A second embodiment of the inventive apparatus in a more detailed diagrammatic representation.

In the apparatus 1' according to the invention shown in FIG. 2 a filtering device 9 is positioned upstream of the pump 3, the same components being given the same reference numerals. Between the pump 3 and an oxidation unit 4', which is indirectly heated in the embodiment shown, is provided an electrochemical reactor 10 for oxygen generation purposes. The condensing unit 7 is connected to the microreactor 4' and is located behind a pump 11 for delivering condensate into and through a flow-through cell 12. Between the condensing unit 7 and the pump 11 is a feed location 13' for the feeding in of phosphoric acid 13. The flow-through cell 12 is connected to an analytical unit 14, such as a measuring cell and a detection unit. The analytical unit 14 can be that known from DE-OS 41 33 300. The flow-through cell 12 is followed by a pressure maintaining valve 15 in the form of a regulating valve. By means of said regulating valve 15 there is a build-up of a pressure p>5 bar by reducing the flow cross-section at the end of said cell 12. The gaseous carbon dioxide is kept in solution by the constantly maintained pressure between the pump 11 and the flow-through cell 12. To the pressure maintaining valve 15 is connected a drain 16, by means of which the fraction of the sample to be investigated flowing freely through the cell 12 can e.g. be returned to the water mains.

In the third embodiment of an inventive apparatus 1" shown in FIG. 3, between the microreactor or oxidation unit 4' and the condensing unit 7 is provided a further regulating valve 17 as the pressure maintaining valve. Through the regulating valve 17 positioned directly behind the microreactor 4', the pressure is built up to p>223 bar by reducing the flow cross-section at the open end of the microreactor 4'. Through the use of such a pressure maintaining valve 17 the geometry of the microreactor 4' can be modified and in particular through an enlargement of the reactor volume longer reaction times can be obtained, because the pressure build-up does not take place through the vapor tension of the aqueous sample in the microreactor 4'.

The TOC value is determined by supercritical wet oxidation. For this purpose, firstly an aqueous test solution 2 to be tested, following filtration and oxygen enrichment, is continuously supplied at a constant flow rate by the high pressure pump 3 to a directly or indirectly heated microreactor 4 or 4'. The microreactor 4, 4' is preferably a heated capillary tube with a small internal diameter. Within the capillary tube 4', 4 the sample or test solution is heated to a predetermined temperature, so that the physical parameters (T>373° C. and p>225 bar) necessary for supercritical wet oxidation are attained. The sample to be investigated is consequently oxidatively transformed at approximately 400° C. and 240 bar, accompanied by oxygen addition. The necessary pressure is built up by the evaporation pressure of the test solution in the interior of the capillary tube or by means of the pressure maintaining valve.

Thus, a continuous transformation of the organic compounds in the test solution is possible. To ensure the complete transformation, oxygen produced in excess by the electrochemical reactor 10 is supplied to the sample solution. This can take place not only, as shown, before, but also during the oxidative transformation. As a result of the reaction conditions within the microreactor 4, 4', the organic compounds in the test solution and the oxygen are completely dissolved. A supercritical state of the aqueous solution in the microreactor is produced. The solubility of the organic compounds to be investigated is significantly increased due to the homogeneous reaction conditions in the microreactor. In this state there is also a drastic increase in the catalytic activity, which improves the reaction kinetics of the oxidation reaction. Oxygen is required as an oxidation aid, so that under the chosen conditions organic compounds are oxidized to carbon dioxide using oxygen. Oxygen must be present in excess to ensure a complete oxidation to carbon dioxide. In the case of an oxygen deficiency, apart from carbon dioxide, other undesired carbon-containing oxidation products may occur.

Oxygen generation preferably takes place electrochemically in a flow-through cell upstream of the reaction capillary. Oxygen is generated by anodic oxidation of water. In the indicated alternative "during supercritical wet oxidation", the electrodes must be integrated into the reactor chamber. A pressure maintaining valve is used for improving the pressure build-up. Through the use of a pressure maintaining valve, it is possible to freely choose the geometry of the reaction chamber and the electrodes.

As the oxidative transformation now takes place in a one-phase system, the reaction conditions here are better controllable than in the known combustion reactions. Through the dosing in of oxygen in excess, the organic compounds are oxidized to carbon dioxide and water. Heteroatoms contained in the hydrocarbon compounds (sulphur, halogens and nitrogen) are converted into the corresponding mineral acids.

Following the oxidative transformation by supercritical wet oxidation, the gaseous sample is condensed in an adequately dimensioned condenser of the condensing unit 7. By means of the pump 11 the condensate or condensed sample 8 is supplied to the flow-through cell 12. A constant pressure is built up between the pump 11 and open end of the cell 12, in order to e.g. maintain in solution the gaseous carbon dioxide. Pressure build-up takes place by means of the pressure maintaining valve 15.

Between the condensing unit 7 and the pump 11, an acid dosing takes place at 13', e.g. of phosphoric acid, so as to convert the hydrogencarbonate and carbonate contained in the sample into free carbonic acid (carbon dioxide). In order to ensure a complete transformation of the hydrogencarbonate and carbonates, the pH-value following acid addition should be pH=2. As the free carbonic acid concentration and the carbonate and hydrogencarbonate concentration are directly dependent on the pH-value and the measuring apparatus used can only detect gaseous substances, for the determination of the carbon dioxide it is necessary to know or keep constant the pH-value. With a non-constant pH-value, the determination of the carbon dioxide can take place by measuring the free carbonic acid (carbon dioxide), as well as a measurement of the pH-value.

The flow-through cell 12 serves as a sample supply system for the analytical unit 14. For this purpose the flow-through cell 12 contains a liquid-impermeable, but gas-permeable membrane, through which at least the gaseous carbon dioxide is sucked off into a measuring cell 14 with a not shown pump, which produces a constant vacuum. A partial flow of the gaseous carbon dioxide passes via a not shown pressure transducer with an adjustable shield to the detection unit 14. By clearly defined temperature and pressure conditions in the flow-through cell 12, the dissolved carbon dioxide quantity in the condensed sample is proportional to the gaseous carbon dioxide quantity in the detection unit 14. For detection purposes use is preferably made of a mass spectrometer. For this purpose the measuring cell has an electron impact ion source of a quadrupole mass spectrometer. By means of the mass spectrometer the total carbon content or TC value is determined. The TOC value of organically bound carbon is then determined by differentiation between the TC value for total carbon and TIC value for inorganically bound carbon:

$$TOC=TC-TIC.$$

The TIC value with respect to carbonates, hydrogencarbonates and free carbonic acid is determined prior to oxidation from the test solution by determining the pH-value.

In a specific example of the method according to the invention a difficultly oxidizable substance, namely N-cetyl-trimethylammonium bromide, was prepared with the means shown in FIG. 1.

Hitherto complete transformation of difficultly oxidizable N-cetyl-trimethylammonium bromide, has only been possible with apparatuses for determining the TOC value with combustion units at high oven temperatures above 850° C. However, the disadvantages referred to hereinbefore then arise.

For transformation with the oxidation unit according to the invention, use was made of an aqueous standard solution of the model substance in the ppm range. Using a commercially available HPLC pump 3 the standard solution 2 was pumped at a constant flow rate into the oxidation unit 4 constructed as a reaction capillary. The reaction capillary 4 simultaneously serving as a heating resistor, i.e. a directly heated oxidation unit, was heated to a clearly defined temperature. Through the heating of the reaction capillary 4, the pressure rise necessary for oxidative transformation was obtained through the evaporation pressure of the standard solution 2. The transformed, gaseous solution was then condensed by a correspondingly dimensioned condenser 7.

The completeness of the oxidative transformation was then checked by a TOC analysis (according to FIG. 2 or 3). Measurements revealed that the model substance had been almost completely transformed without any oxygen addition.

We claim:

1. Method for the continuous determination of gaseous oxidation products from industrial process, drinking and/or waste water, and for determining a total organic carbon (TOC) value, comprising, continuously pumping at least organically bound carbon of organic components contained in a test solution to be investigated into a microreactor, heating said test solution to a predetermined temperature, and continuously transforming said organic compounds in the test solution by super critical wet oxidation under a temperature of more than 373° C. of more than 225 bar ($22.5 \times 10^5$ pa) and pressure, wherein gaseous oxidation products are supplied to a measuring unit where at least organically bound carbon is detected.

2. Method according to claim 1, characterized in that the elevated pressure is built up by the evaporation pressure of the test solution.

3. Method according to claim 1, characterized in that increased pressure in the microreactor is maintained by controlling a pressure maintaining valve.

4. Method according to claim 1 or 2, characterized in that oxygen is supplied to the test solution.

5. Method according to claim 4, characterized in that the oxygen is electrochemically generated.

6. Method according to claim 1 or 2, characterized in that the gaseous sample produced in the microreactor is condensed.

7. Method according to claim 6, characterized in that acid is dosed into the condensed sample.

8. Method according to claim 6, characterized in that the condensed sample is passed with a constant flow rate and under a constant pressure through a flow-through cell.

9. Method according to claim 8, characterized in that the condensed sample is led past a liquid-impermeable, but gas-permeable membrane, the gaseous oxidation products in the gas phase thereof being sucked from the sample through the membrane and passed through a measuring cell.

10. Method according to claim 9, characterized in that in the vicinity of the membrane, the sample is kept at a constant temperature and a predetermined pressure.

11. Method according to claim 8, characterized in that a proportion of the gaseous oxidation products to be investigated passes from an area of slight underpressure, via a pressure transducer to a detection unit.

12. Method according to claim 8, characterized in that the gaseous oxidation products are measured by means of a mass spectrometer.

13. The method of claim 1, wherein said method allows for the direct determination of volatile oxidation products from the test solution without prior phase transfer.

* * * * *